United States Patent [19]

Smith

[11] 4,126,753
[45] Nov. 21, 1978

[54] CIS-4,5-DIDEHYDRO-13,14-DIDEHYDRO-11-DEOXY-PGF$_1\alpha$ COMPOUNDS

[75] Inventor: Herman W. Smith, Kalamazoo, Mich.

[73] Assignee: The Upjohn Company, Kalamazoo, Mich.

[21] Appl. No.: 820,973

[22] Filed: Aug. 1, 1977

Related U.S. Application Data

[62] Division of Ser. No. 657,740, Feb. 13, 1976.

[51] Int. Cl.$^2$ .......................................... C07C 177/00
[52] U.S. Cl. ..................................... 560/121; 260/408; 260/410; 260/410.5; 260/410.9 R; 260/413; 562/503
[58] Field of Search ................... 560/121; 260/514 D, 260/408, 410, 410.5, 410.9 R, 413

[56] References Cited

PUBLICATIONS

Fried et al., Proc. Nat. Acad. Sci., 70, 1579 (1973).

Primary Examiner—Robert Gerstl
Attorney, Agent, or Firm—Robert A. Armitage

[57] ABSTRACT

This invention comprises certain analogs of the prostaglandins in which the double bond between C-13 and C-14 is replaced by a triple bond. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

73 Claims, No Drawings

CIS-4,5-DIDEHYDRO-13,14-DIDEHYDRO-11-DEOXY-PGF$_1\alpha$ COMPOUNDS

The present application is a divisional application of Ser. No. 657,740, filed Feb. 13, 1976, now pending issuance as a United States Patent.

The present invention relates to prostaglandin analogs, for which the essential material constituting disclosure therefor is incorporated by reference here from Ser. No. 820,974, filed Aug. 1, 1977, now U.S. Pat. No. 4,099,015, issued July 4, 1978 which is a divisional application of Ser. No. 657,740.

I claim:

1. A prostaglandin analog of the formula

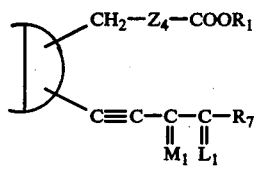

wherein D is

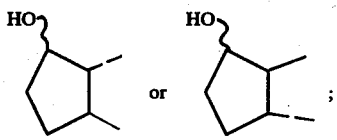

wherein $Z_4$ is
cis—$CH_2$—CH=CH—$(CH_2)_g$—$CH_2$—, wherein $g$ is 1, 2, or 3;
wherein $R_7$ is
—$(CH_2)_m$—$CH_3$, wherein $m$ is 1 to 5, inclusive;
wherein $L_1$ is

or a mixture of

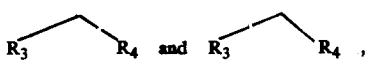

wherein $R_3$ and $R_4$ are hydrogen, methyl, or fluoro, being the same or different, with the provisio that one of $R_3$ and $R_4$ is methyl only when the other is hydrogen or methyl;
wherein $M_1$ is

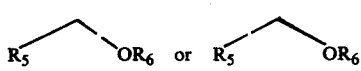

wherein $R_5$ and $R_6$ are hydrogen or methyl, with the proviso that one of $R_5$ and $R_6$ is methyl only when the other is hydrogen; and
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A compound according to claim 1, wherein D is

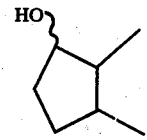

3. A compound according to claim 2, wherein $M_1$ is

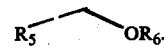

4. A compound according to claim 3, wherein $g$ is 1.
5. A compound according to claim 4, wherein $R_3$, $R_4$, $R_5$, and $R_6$ are all hydrogen.
6. 15-epi-cis-4,5-Didehydro-13,14-didehydro-8$\beta$, 12$\alpha$-11-deoxy-PGF$_1\alpha$, methyl ester, a compound according to claim 4.
7. A compound according to claim 2, wherein $M_1$ is

8. A compound according to claim 7, wherein $g$ is 3.
9. A compound according to claim 7, wherein $g$ is 1.
10. A compound according to claim 9, wherein $R_3$ and $R_4$ are both hydrogen.
11. A compound according to claim 10, wherein $R_5$ is methyl.
12. cis-4,5-Didehydro-15-methyl-13,14-didehydro-8$\beta$, 12$\alpha$-11-deoxy-PGF$_1\alpha$, a compound according to claim 11.
13. cis-4,5-Didehydro-15-methyl-13,14-didehydro-8$\beta$,12$\alpha$-11-deoxy-PGF$_1\alpha$, methyl ester, a compound according to claim 11.
14. A compound according to claim 10, wherein $R_6$ is methyl.
15. cis-4,5-Didehydro-13,14-didehydro-8$\beta$, 12$\alpha$-11-deoxy-PGF$_1\alpha$, 15-methyl ether, a compound according to claim 14.
16. cis-4,5-Didehydro-13,14-didehydro-8$\beta$, 12$\alpha$-11-deoxy-PGF$_1\alpha$, methyl ester, 15-methyl ether, a compound according to claim 14.
17. A compound according to claim 10, wherein $R_5$ and $R_6$ are both hydrogen.
18. cis-4,5-Didehydro-13,14-didehydro-8$\beta$, 12$\alpha$-11-deoxy-PGF$_1\alpha$, a compound according to claim 17.
19. cis-4,5-Didehydro-13,14-didehydro-8$\beta$, 12$\alpha$-11-deoxy-PGF$_1\alpha$, methyl ester, a compound according to claim 17.
20. A compound according to claim 9, wherein at least one of $R_3$ and $R_4$ is methyl.
21. A compound according to claim 20, wherein $R_3$ and $R_4$ are both methyl.
22. A compound according to claim 21, wherein $R_5$ is methyl.
23. cis-4,5-Didehydro-15,16,16-trimethyl-13,14-didehydro-8$\beta$, 12$\alpha$-11-deoxy-PGF$_1\alpha$, methyl ester, a compound according to claim 22.
24. A compound according to claim 21, wherein $R_6$ is methyl.
25. cis-4,5-Didehydro-16,16-dimethyl-13,14-didehydro-8$\beta$, 12$\alpha$-11-deoxy-PGF$_1\alpha$, methyl ester, 15-methyl ether, a compound according to claim 24.
26. A compound according to claim 21, wherein $R_5$ and $R_6$ are both hydrogen.

27. cis-4,5-Didehydro-16,16-dimethyl-13,14-didehydro-8β, 12α-11-deoxy-PGF$_1$α, a compound according to claim 26.

28. cis-4,5-Didehydro-16,16-dimethyl-13,14-didehydro-8β, 12α-11-deoxy-PGF$_1$α, methyl ester, a compound according to claim 26.

29. A compound according to claim 9, wherein at least one of R$_3$ and R$_4$ is fluoro.

30. A compound according to claim 29, wherein R$_3$ and R$_4$ are both fluoro.

31. A compound according to claim 30, wherein R$_5$ is methyl.

32. cis-4,5-Didehydro-15-methyl-16,16-difluoro-13,14-didehydro-8β, 12α-11-deoxy-PGF$_1$α, methyl ester, a compound according to claim 31.

33. A compound according to claim 30, wherein R$_6$ is methyl.

34. cis-4,5-Didehydro-16,16-difluoro-13,14-didehydro-8β, 12α-11-deoxy-PGF$_1$α, methyl ester, 15-methyl ether, a compound according to claim 33.

35. A compound according to claim 30, wherein R$_5$ and R$_6$ are both hydrogen.

36. cis-4,5-Didehydro-16,16-difluoro-13,14-didehydro-8β, 12α-11-deoxy-PGF$_1$α, a compound according to claim 35.

37. cis-4,5-Didehydro-16,16-difluoro-13,14-didehydro-8β, 12α-11-deoxy-PGF$_1$α, methyl ester, a compound according to claim 35.

38. A compound according to claim 1, wherein D is

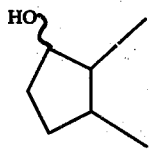

39. A compound according to claim 38, wherein M$_1$ is

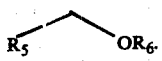

40. A compound accordng to claim 39, wherein g is .

41. A compound according to claim 40, wherein R$_3$, R$_4$, R$_5$, and R$_6$ are all hydrogen.

42. 15-epi-cis-4,5-Didehydro-13,14-didehydro-11-deoxy-17-PGF$_1$α, methyl ester, a compound according to claim 41.

43. A compound according to claim 38, wherein M$_1$ is

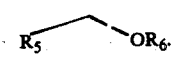

44. A compound according to claim 43, wherein g is 3.

45. A compound according to claim 43, wherein g is 1.

46. A compound according to claim 45, wherein R$_3$ and R$_4$ are both hydrogen.

47. A compound according to claim 46, wherein R$_5$ is methyl.

48. cis-4,5-Didehydro-15-methyl-13,14-didehydro-11-deoxy-17-PGF$_1$α, a compound according to claim 47.

49. cis-4,5-Didehydro-15-methyl-13,14-didehydro-11-deoxy-PGF$_1$α, methyl ester, a compound according to claim 47.

50. A compound according to claim 46, wherein R$_6$ is methyl.

51. cis-4,5-Didehydro-13,14-didehydro-11-deoxy-PGF$_1$α, 15-methyl ether, a compound according to claim 50.

52. cis-4,5-Didehydro-13,14-didehydro-11-deoxy-PGF$_1$α, methyl ester, 15-methyl ether, a compound according to claim 50.

53. A compound according to claim 46, wherein R$_5$ and R$_6$ are both hydrogen.

54. cis-4,5-Didehydro-13,14-didehydro-11-deoxy-PGF$_1$α, a compound according to claim 53.

55. cis-4,5-Didehydro-13,14-didehydro-11-deoxy-PGF$_1$α, methyl ester, a compound according to claim 53.

56. A compound according to claim 45, wherein at least one of R$_3$ and R$_4$ is methyl.

57. A compound according to claim 56, wherein R$_3$ and R$_4$ are both methyl.

58. A compound according to claim 57, wherein R$_5$ is methyl.

59. cis-4,5-Didehydro-15,16,16-trimethyl-13,14-didehydro-11-deoxy-PGF$_1$α, methyl ester, a compound according to claim 58.

60. A compound according to claim 57, wherein R$_6$ is methyl.

61. cis-4,5-Didehydro-16,16-dimethyl-13,14-didehydro-11-deoxy-PGF$_1$α, methyl ester, 15-methyl ether, a compound according to claim 60.

62. A compound according to claim 57, wherein R$_5$ and R$_6$ are both hydrogen.

63. cis-4,5-Didehydro-16,16-dimethyl-13,14-didehydro-11-deoxy-PGF$_1$α, a compound according to claim 62.

64. cis-4,5-Didehydro-16,16-dimethyl-13,14-didehydro-11-deoxy-PGF$_1$α, methyl ester, a compound according to claim 62.

65. A compound according to claim 45, wherein at least one of R$_3$ and R$_4$ is fluoro.

66. A compound according to claim 65, wherein R$_3$ and R$_4$ are both fluoro.

67. A compound according to claim 66, wherein R$_5$ is methyl.

68. cis-4,5-Didehydro-15-methyl-16,16-difluoro-13,14-didehydro-11-deoxy-PGF$_1$α, methyl ester, a compound according to claim 67.

69. A compound according to claim 66, wherein R$_6$ is methyl.

70. cis-4,5-Didehydro-16,16-difluoro-13,14-didehydro-11-deoxy-PGF$_1$α, methyl ester, 15-methyl ether, a compound according to claim 69.

71. A compound according to claim 66, wherein R$_5$ and R$_6$ are both hydrogen.

72. cis-4,5-Didehydro-16,16-difluoro-13,14-didehydro-11-deoxy-PGF$_1$α, a compound according to claim 71.

73. cis-4,5-Didehydro-16,16-difluoro-13,14-didehydro-11-deoxy-PGF$_1$α, methyl ester, a compound according to claim 71.

* * * * *

UNITED STATES PATENT OFFICE
CERTIFICATE OF CORRECTION

Patent No. 4,126,753    Dated November 21, 1978

Inventor(s) Herman W. Smith

It is certified that error appears in the above-identified patent and that said Letters Patent are hereby corrected as shown below:

Column 3, line 50, "deoxy-17-$PGF_1\alpha$," should read -- deoxy-$PGF_1\alpha$, --;
Column 4, line 2, "deoxy-17-$PGF_1\alpha$," should read -- deoxy-$PGF_1\alpha$, --.

Signed and Sealed this

Twenty-seventh Day of March 1979

[SEAL]

Attest:

RUTH C. MASON
Attesting Officer

DONALD W. BANNER
Commissioner of Patents and Trademarks